US007263155B2

(12) United States Patent
Matsuura

(10) Patent No.: US 7,263,155 B2
(45) Date of Patent: Aug. 28, 2007

(54) RADIOGRAPHY APPARATUS AND RADIATION IMAGE PROCESSING METHOD

(75) Inventor: Tomohiko Matsuura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 51 days.

(21) Appl. No.: 10/946,431

(22) Filed: Sep. 21, 2004

(65) Prior Publication Data

US 2005/0111615 A1 May 26, 2005

(30) Foreign Application Priority Data

Sep. 22, 2003 (JP) ............................. 2003-329381

(51) Int. Cl.
*G01N 23/087* (2006.01)

(52) U.S. Cl. ............................................. 378/4; 378/20

(58) Field of Classification Search ............. 378/4–20, 378/62, 901
See application file for complete search history.

(56) References Cited

U.S. PATENT DOCUMENTS 5,164,971 A * 11/1992 Peyret et al. .................. 378/4
5,933,473 A * 8/1999 Kitaguchi et al. ............ 378/57
6,345,028 B1 * 2/2002 Jaeger ......................... 369/84
6,373,916 B1 * 4/2002 Inoue et al. ................... 378/4
2001/0043732 A1 11/2001 Matsuura

FOREIGN PATENT DOCUMENTS

JP 05-007579 A 1/1993
JP 2525648 B 5/1996

* cited by examiner

*Primary Examiner*—Hoon Song

(57) ABSTRACT

A plurality of pieces of image data processed by a preprocessed circuit are sequentially received and at least one representative image is selected from among the plurality of pieces of image data by a representative image selection circuit. For example, one piece of image data out of every 250 pieces of image data is selected from among 1000 pieces of acquired image data to select four pieces of image data as representative images. An irradiated area extraction circuit extracts X-ray irradiated areas of the representative images. A reconstruction area determination circuit determines a CT reconstruction area on the basis of the X-ray irradiated areas. The reconstruction circuit reconstructs CT images from all or part of the acquired image data on the basis of the CT reconstruction area.

14 Claims, 16 Drawing Sheets

| No. | SAMPLING PATTERN | RADIOGRAPHING DIRECTION |
|---|---|---|
| 0 |  | 0.0 |
| ⋮ | ⋮ | ⋮ |
| 4 |  | 90.0 |
| ⋮ | ⋮ | ⋮ |
| 15 | | 337.5 |

RADIOGRAPHY APPARATUS AND RADIATION IMAGE PROCESSING METHOD

CROSS REFERENCE TO RELATED APPLICATIONS

This application claims the benefit of Japanese Application No. 2003-329381, filed Sep. 22, 2003, the entire contents of which is incorporated herein by reference.

BACKGROUND OF THE INVENTION

1. Field of the Invention

The present invention relates to radiography apparatuses for performing computer tomography (CT) reconstruction on a plurality of pieces of image data, and more particularly, to a radiography apparatus for determining a CT reconstruction area on the basis of an X-ray irradiated area of the image data.

2. Description of the Related Art

FIG. 16 schematically illustrates a known technology. CT reconstruction is performed using a plurality of pieces of image data 001 as input image data, and CT images 002, which are tomograms, are acquired. Representative image data 003 is one piece of image data included in the image data 001. A CT reconstruction area 004 is designated by a radiographer.

In order to acquire the CT images 002 from the image data 001, a CT reconstruction area must be determined. The following three procedures are known as the main procedures for determining a CT reconstruction area:

(A) Perform CT reconstruction on the whole image data as a reconstruction area without designating a reconstruction area;

(B) Perform reconstruction using a fixed reconstruction area determined in advance; and (C) Perform CT reconstruction by using the representative image data 003 from among the plurality of pieces of image data 001 as a scanogram and designating the CT reconstruction area 004 by a radiographer, as described in Japanese Patent Laid-Open No. 2000-316840.

However, according to procedure (A) in which the whole image data is used as a reconstruction area, an increased computation time is necessary for CT reconstruction and a CT image of an area unnecessary for diagnosis is generated. Thus, diagnosis efficiency may be reduced. Also, according to procedure (B) in which a fixed reconstruction area is used, a CT image of an area necessary for diagnosis may not be acquired depending on the influence of the position or shape of a patient. Also, a CT image of an area unnecessary for diagnosis may be generated. Furthermore, according to procedure (C) in which a radiographer designates a reconstruction area, the radiographer must manually perform a troublesome operation. This manual operation reduces the throughput of CT radiography.

SUMMARY OF THE INVENTION

In order to solve the above problems, an object of the present invention is to provide a radiography apparatus that can perform CT reconstruction only on an area necessary for diagnosis in a short time without requiring a radiographer to perform a troublesome manual operation and that enhances throughput of CT radiography when CT images are acquired from a plurality of pieces of image data.

According to one aspect of the present invention, there is provided a radiography apparatus including a radiation source for emitting radiation to a test object; a rotating device for rotating the test object during radiation; a two-dimensional X-ray sensor for converting the radiation to electrical signals; a processing circuit for converting the electrical signals into a plurality of pieces of image data; and a reconstruction circuit for performing computer tomography reconstruction from the plurality of pieces of image data obtained by radiographing the test object from different directions. A reconstruction area for the computer tomography reconstruction is determined on the basis of an image area corresponding to an irradiated area of at least one piece of image data.

Other features and advantages of the present invention will be apparent from the following description taken in conjunction with the accompanying drawings, in which like reference characters designate the same or similar parts throughout the figures.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE PREFERRED EMBODIMENTS

Preferred embodiments of the present invention will now be described in detail in accordance with the accompanying drawings.

Figure 1:
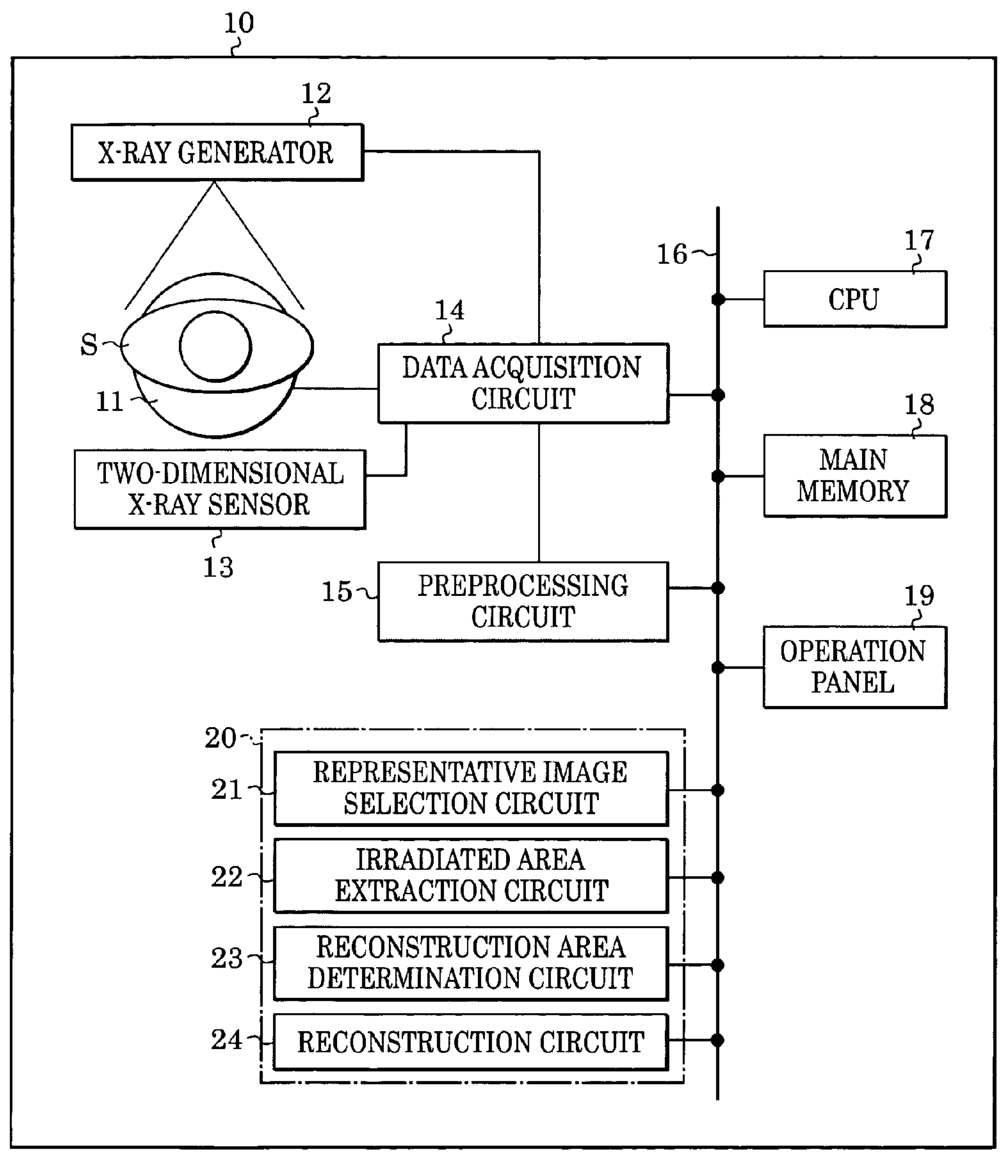
FIG. 1 shows the structure of a radiography apparatus according to a first embodiment of the present invention.

FIG. 1 shows the structure of a radiography apparatus 10 according to a first embodiment of the present invention having an image processing function. An X-ray generator 12 and a two-dimensional X-ray sensor 13 are arranged so as to sandwich a test object S disposed on a rotating device 11.

The rotating device 11, the X-ray generator 12, and the two-dimensional X-ray sensor 13 are connected to a data acquisition circuit 14.

The data acquisition circuit 14 is connected to a preprocessing circuit 15. Also, the data acquisition circuit 14 and the preprocessing circuit 15 are connected to a central processing unit (CPU) bus 16. The CPU bus 16 is connected to a CPU 17, a main memory 18, an operation panel 19, a representative image selection circuit 21 for selecting at least one representative image from among a plurality of pieces of image data, an irradiated area extraction circuit 22 for acquiring an X-ray irradiated area, a reconstruction area determination circuit 23 for determining a CT reconstruction area based on the X-ray irradiated area, and a reconstruction circuit 24 for performing CT reconstruction in accordance with the reconstruction area. The representative image selection circuit 21, the irradiated area extraction circuit 22, the reconstruction area determination circuit 23, and the reconstruction circuit 24 are included in an image processing circuit 20.

In the radiography apparatus 10, various types of data necessary for processing by the CPU 17 and a work memory for operation of the CPU 17 are stored in the main memory 18. The CPU 17 performs operation control and the like of the whole apparatus using the main memory 18 in accordance with operation by the operation panel 19. The radiography apparatus 10 operates as described below.

The rotating device 11 is set to an operation state to rotate the test object S on the rotating device 11. The test object S is irradiated with an X-ray beam by the X-ray generator 12. The X-ray beam emitted from the X-ray generator 12 penetrates, while being attenuated, the test object S, which is, for example, the chest of a human body, to the two-dimensional X-ray sensor 13, and is output as an X-ray image.

The data acquisition circuit 14 converts the X-ray image output from the two-dimensional X-ray sensor 13 into an electrical signal, and supplies the electrical signal to the preprocessing circuit 15. The preprocessing circuit 15 performs preprocessing, such as offset correction or gain correction, on the X-ray image signal from the data acquisition circuit 14. The preprocessed X-ray image signal is transferred as image data to the main memory 18 and the image processing circuit 20 via the CPU bus 16 under the control of the CPU 17.

As described above, the operations from radiation of an X-ray beam to transfer of image data are repeatedly performed while operating the rotating device 11, so that image data radiographed from different directions is sequentially transferred to the image processing circuit 20.

Figure 2:
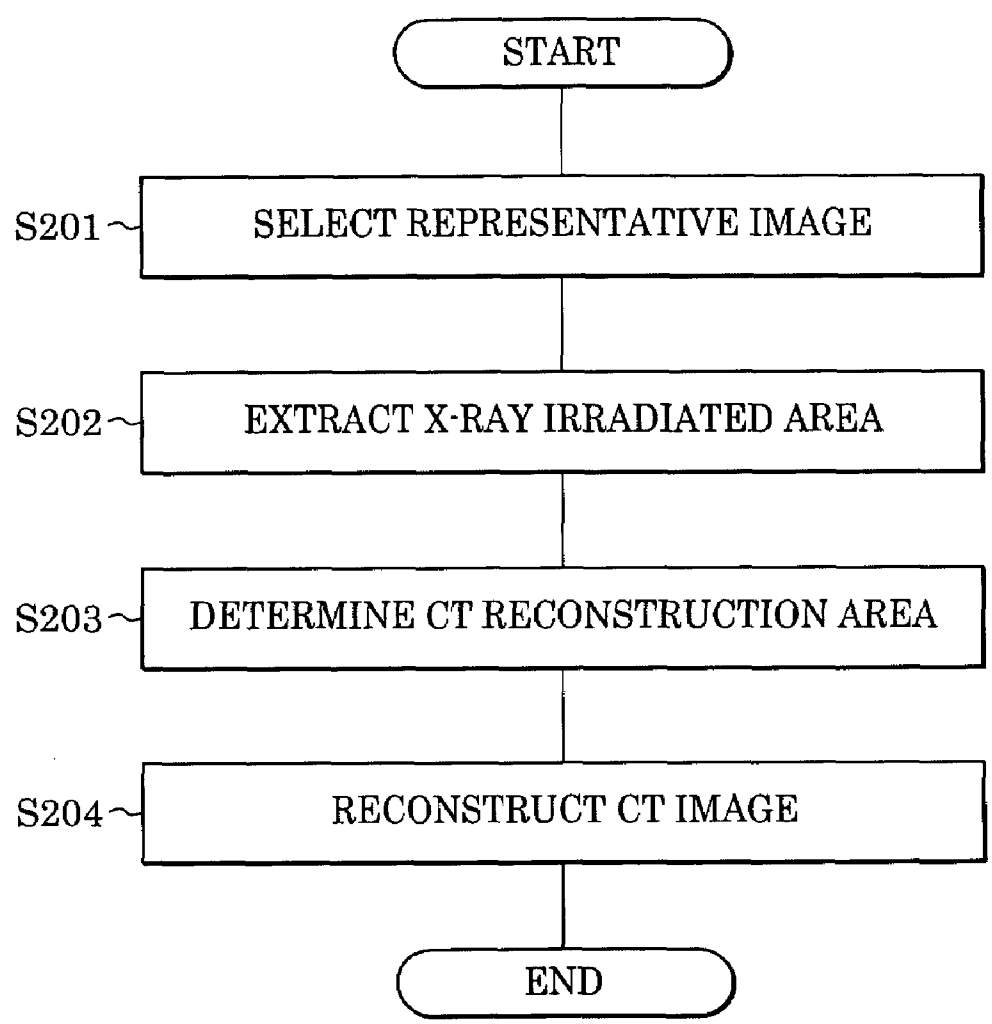
FIG. 2 is a flowchart showing a process performed in the first embodiment.
Figure 3:
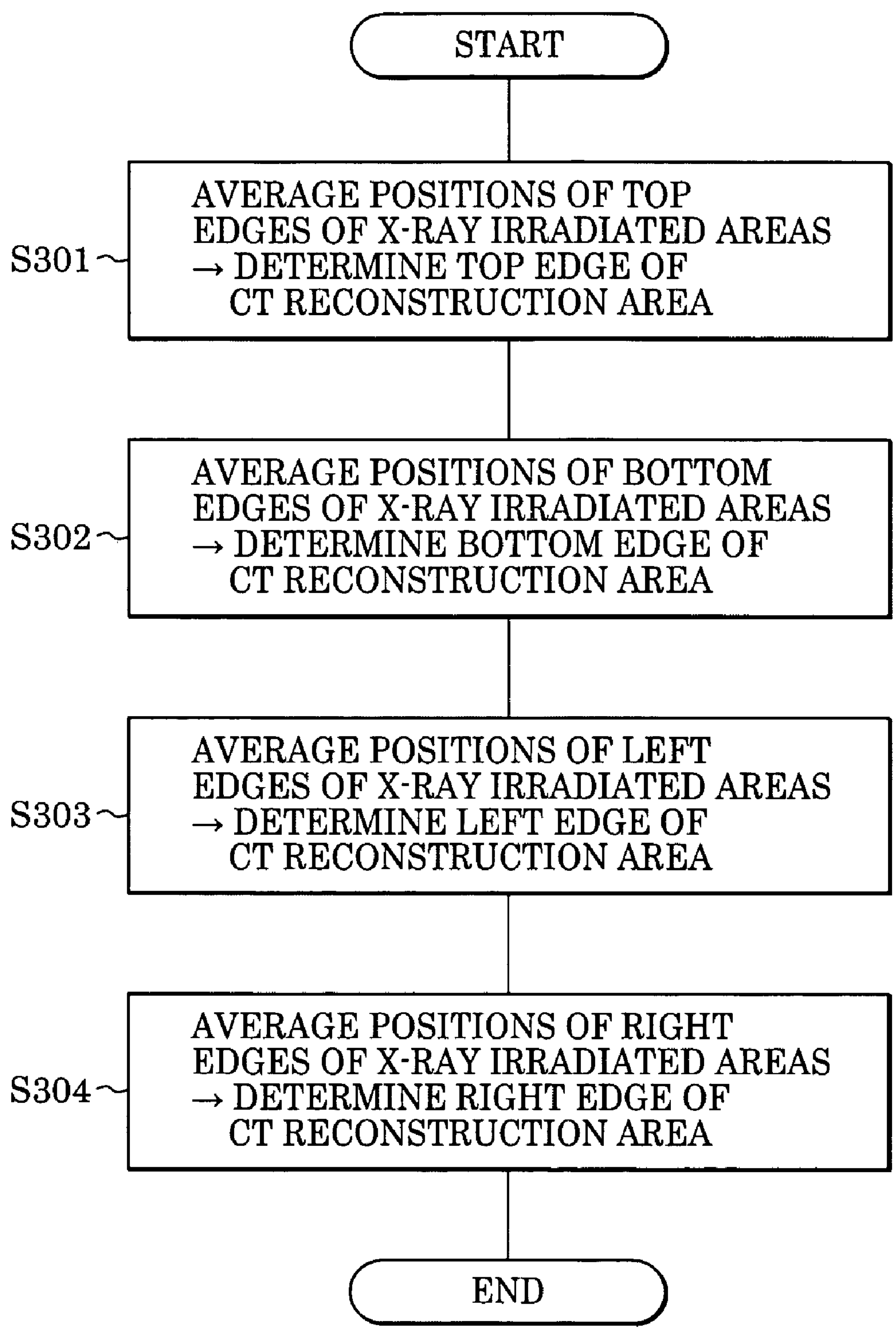
FIG. 3 is a flowchart showing a process performed by a reconstruction area determination circuit.
Figure 4:
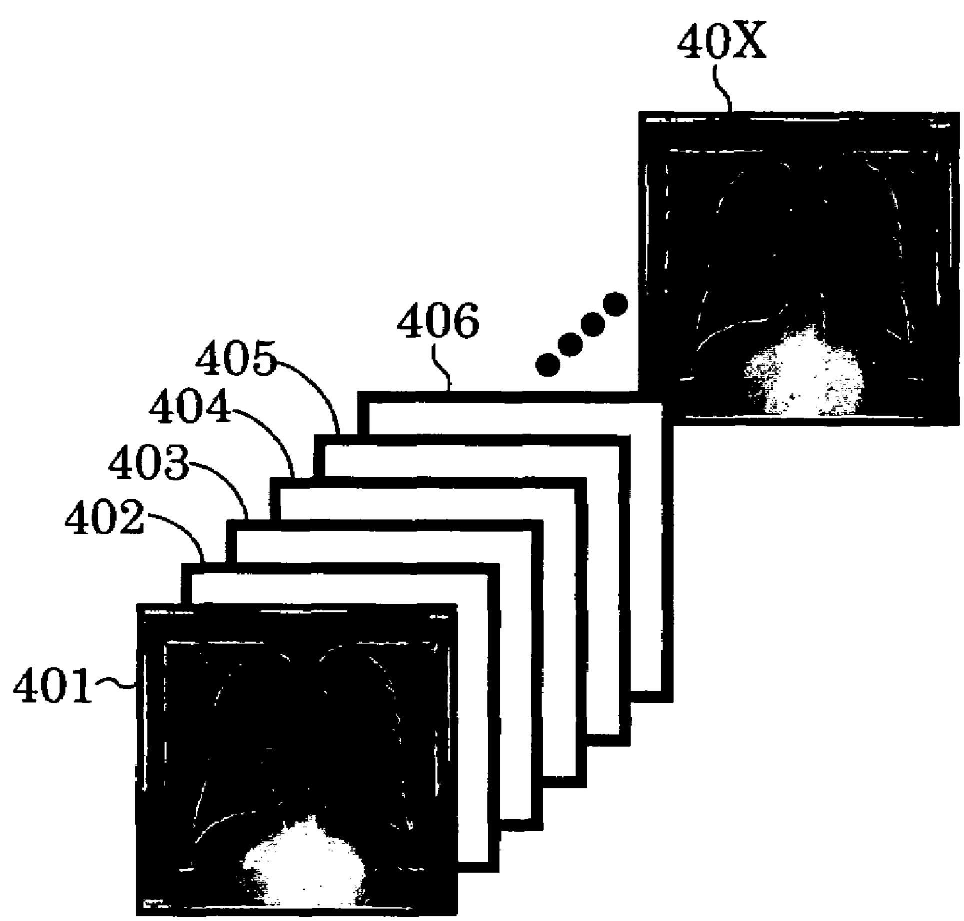
FIG. 4 shows a plurality of pieces of image data.
Figure 5:
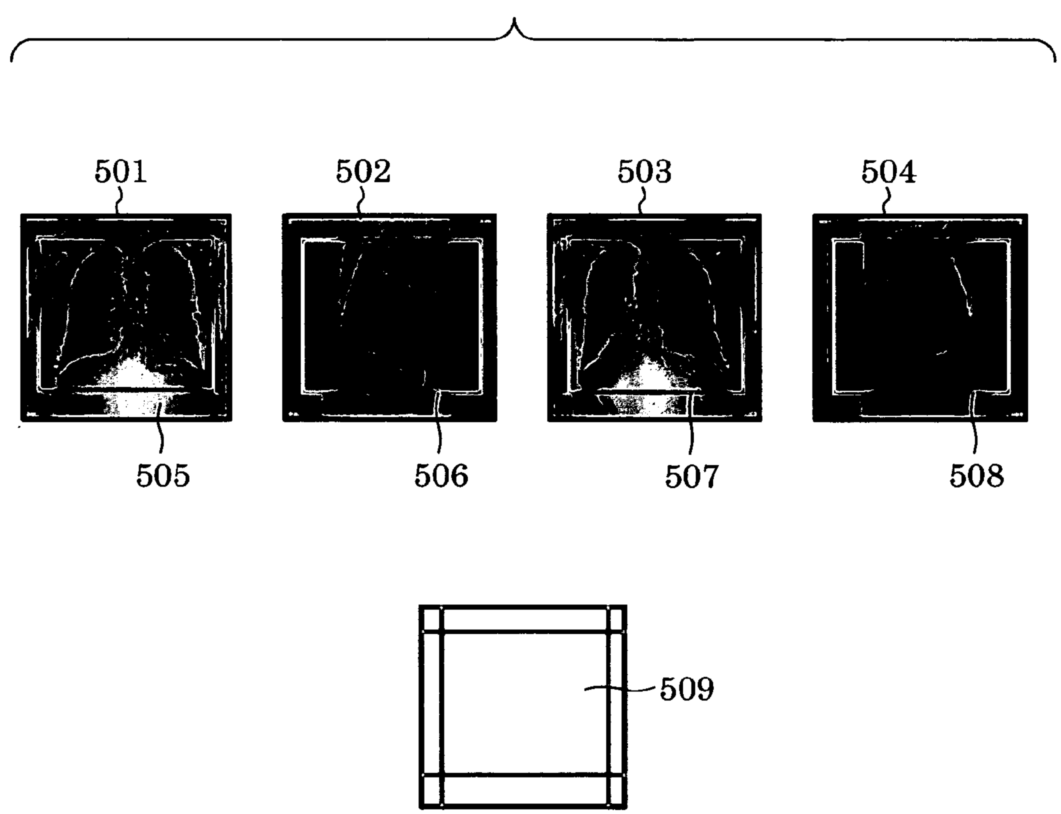
FIG. 5 shows representative images.
Figure 6:
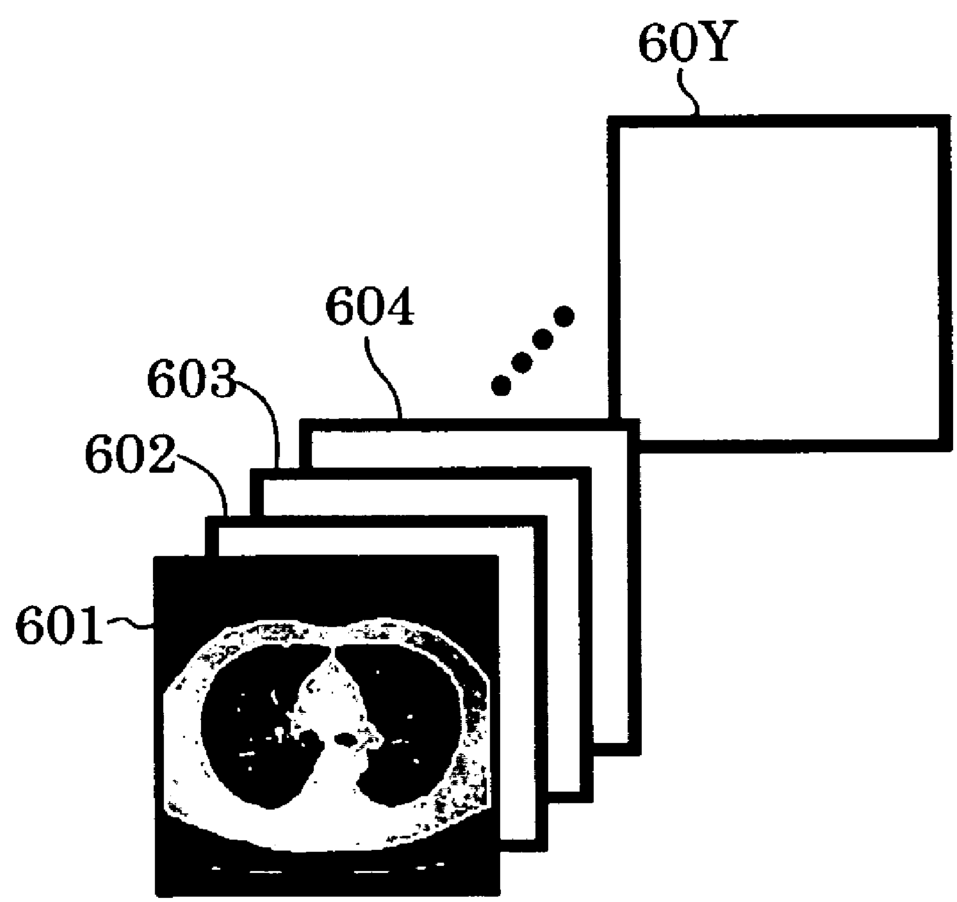
FIG. 6 shows CT images.

FIG. 2 is a flowchart showing a process performed in the first embodiment. FIG. 3 is a flowchart showing a process performed by the reconstruction area determination circuit 23. FIG. 4 shows a plurality of pieces of image data 401 to 40X radiographed from different directions. In FIG. 5, selected representative images 501 to 504, X-ray irradiated areas 505 to 508 acquired from the respective representative images 501 to 504, and a CT reconstruction area 509 obtained by taking the averages of the positions of the top edges, bottom edges, left edges, and right edges of the X-ray irradiated areas 505 to 508 of the representative images 501 to 504 are shown. FIG. 6 shows CT images 601 to 60Y obtained by CT reconstruction.

A process performed by the image processing circuit 20 will now be described with reference to FIG. 2. After sequentially receiving the plurality of pieces of image data 401 to 40X shown in FIG. 4 processed by the preprocessing circuit 15 via the CPU bus 16 under the control of the CPU 17, the image processing circuit 20 selects at least one representative image from among the plurality of pieces of image data by the representative image selection circuit 21 (step S201). The method for selecting a representative image is not particularly limited. For example, the K-th image data may be set as a representative image by using a predetermined constant K or image data from the M-th image data to the N-th image data may be set as representative images by using predetermined constants M and N ($M<N$). Alternatively, the whole image data may be set as representative images. Here, for example, one piece of image data out of every 250 pieces of image data is selected from among 1000 pieces of acquired image data, and four pieces of image data are selected as the representative images 501 to 504, as shown in FIG. 5.

The irradiated area extraction circuit 22 extracts the X-ray irradiated areas 505 to 508 of the representative images 501 to 504 (step S202). The method for extracting an X-ray irradiated area is not particularly limited. A method for detecting characteristics having edge components from a difference in pixel values of two adjacent pixels in an image and extracting an X-ray irradiated area on the basis of the detected characteristics is described in Japanese Patent No. 2525648. Also, a method for dividing an image area into small parts and extracting an X-ray irradiated area on the basis of a density distribution value in the small parts is described in Japanese Patent Laid-Open No. 5-7579. Also, a method for extracting an X-ray irradiated area on the basis of a geometric pattern of edge candidates representing edges of an X-ray irradiated area is described in Japanese Patent Laid-Open No. 2001-307064. In addition, a method for acquiring information on an irradiation aperture of the X-ray generator 12 via the data acquisition circuit 14 is possible. The irradiated area extraction circuit 22 can be realized using any method described above.

The reconstruction area determination circuit 23 determines the CT reconstruction area 509 from the X-ray irradiated areas 505 to 508 (step S203). The processing performed in step S203 is shown in the flowchart of FIG. 3. The average of the positions of the top edges of the X-ray irradiated areas 505 to 508 is taken to determine the top edge of the CT reconstruction area 509 (step S301). Then, the averages of the positions of the bottom edges, left edges, and right edges of the X-ray irradiated areas 505 to 508 are taken to determine the bottom edge, the left edge, and the right edge of the CT reconstruction area 509 (steps S302 to S304). Although the average of each of the edges of the X-ray irradiated areas 505 to 508 is used in steps S301 to S304, it is obvious that for example, a method for using X-ray irradiated edges that are farthest away from the center of an image is also possible.

The reconstruction circuit 24 reconstructs the CT images 601 to 60Y, in accordance with the CT reconstruction area 509, from all or part of the acquired image data 401 to 40X (step S204), as shown in FIG. 6. Since a method for acquiring CT images from image data by CT reconstruction is generally known, an explanation for the method is omitted here.

As described above, according to the first embodiment, a CT reconstruction area is automatically determined on the basis of a position of an X-ray irradiated area of a representative image. Thus, the number of operations to be performed by a radiographer is reduced and throughput of CT radiography is enhanced. Also, since only a part necessary for diagnosis is reconstructed, the computation time is reduced. Furthermore, since a part unnecessary for diagnosis is not reconstructed, diagnosis efficiency is increased.

Figure 7:
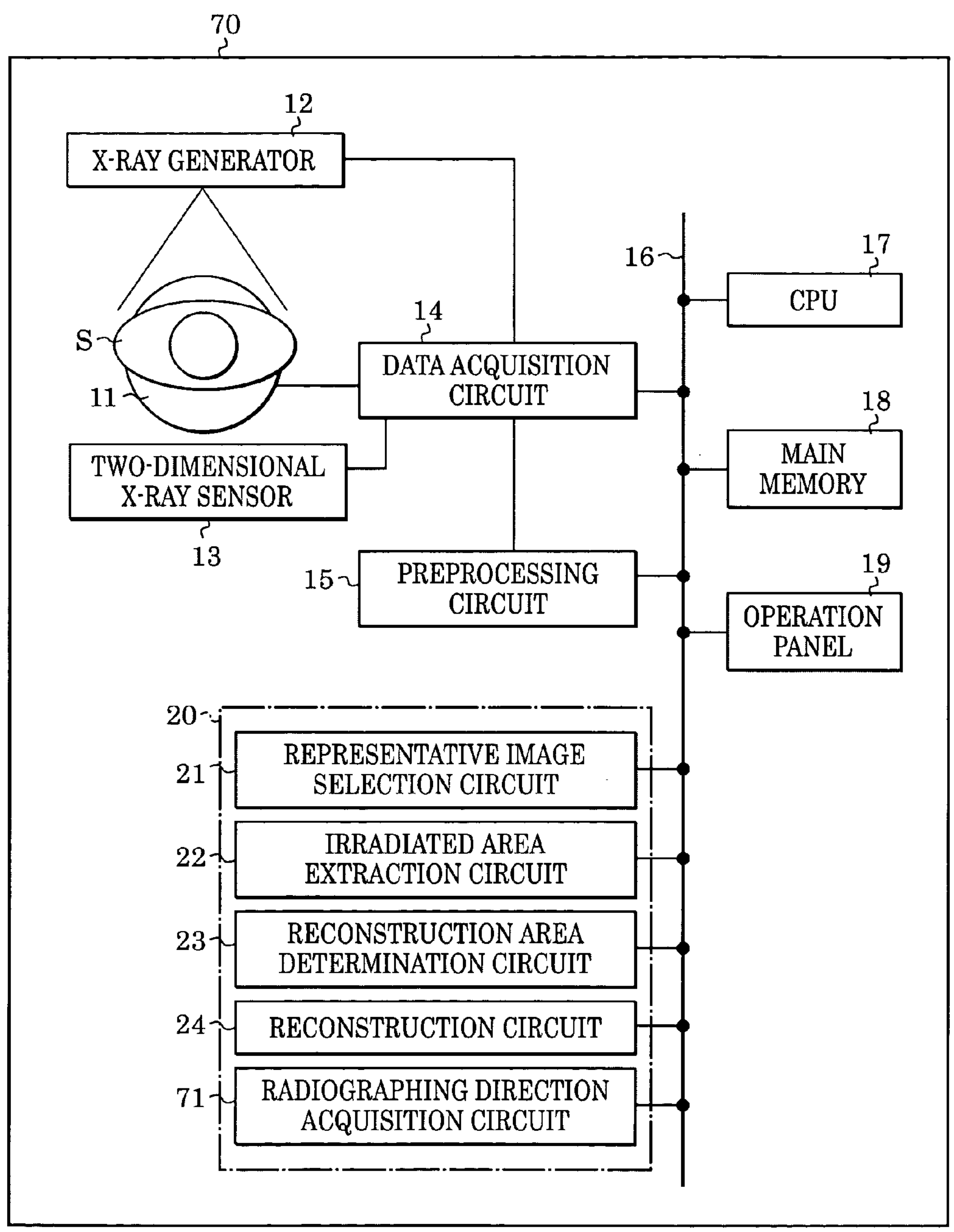
FIG. 7 shows the structure of a radiography apparatus according to a second embodiment of the present invention.

FIG. 7 shows the structure of a radiography apparatus 70 according to a second embodiment of the present invention. The radiography apparatus 70 according to the second embodiment is different from the radiography apparatus 10 according to the first embodiment in that a radiographing direction acquisition circuit 71 is added in the image processing circuit 20. The same reference numerals as in FIG. 1 represent the same members as in FIG. 1. Only the radiographing direction acquisition circuit 71 and related parts will be described.

As in the first embodiment, the operations from radiation of an X-ray beam to transfer of image data are repeatedly performed while operating the rotating device 11, so that image data radiographed from different directions is sequentially transferred to the image processing circuit 20.

Figure 8:
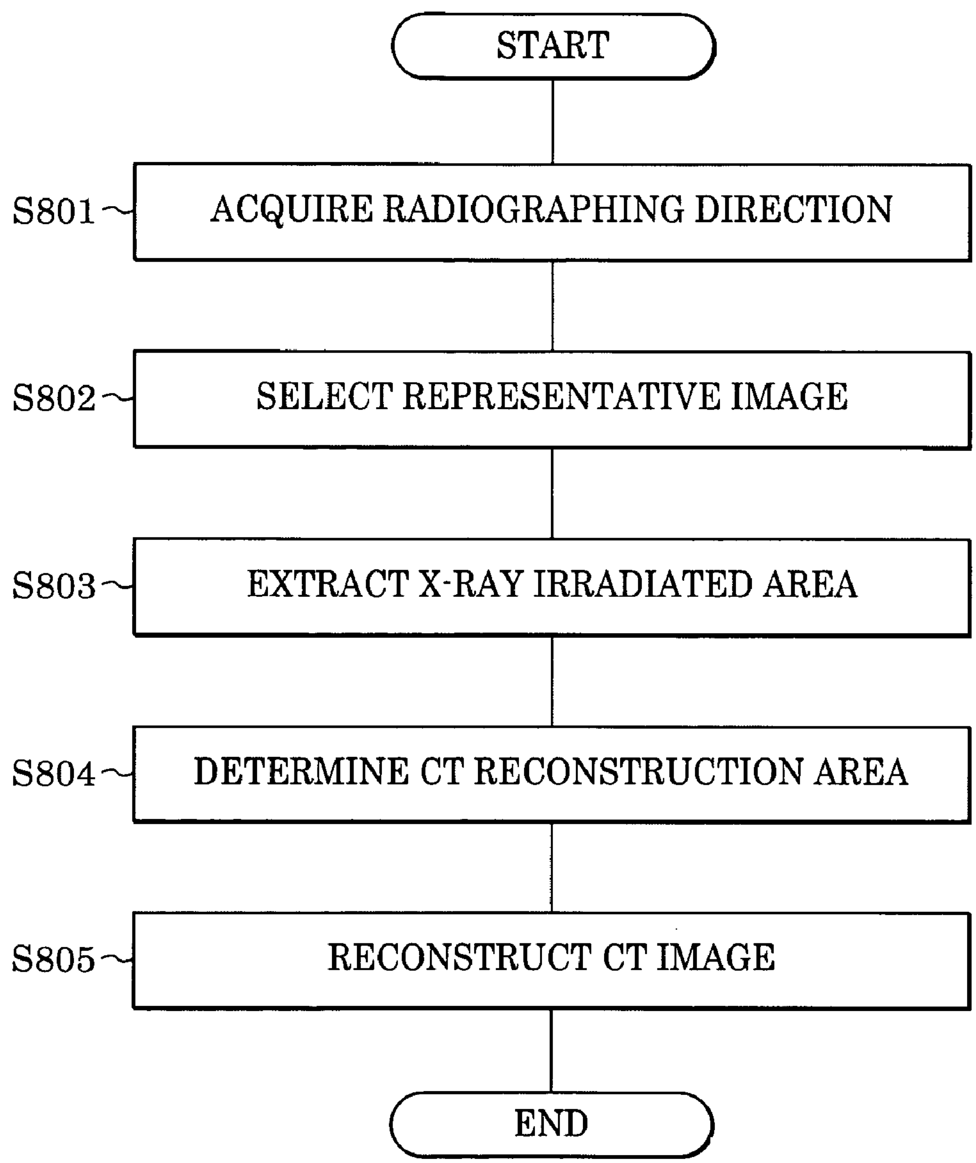
FIG. 8 is a flowchart showing a process performed in the second embodiment.
Figure 9:
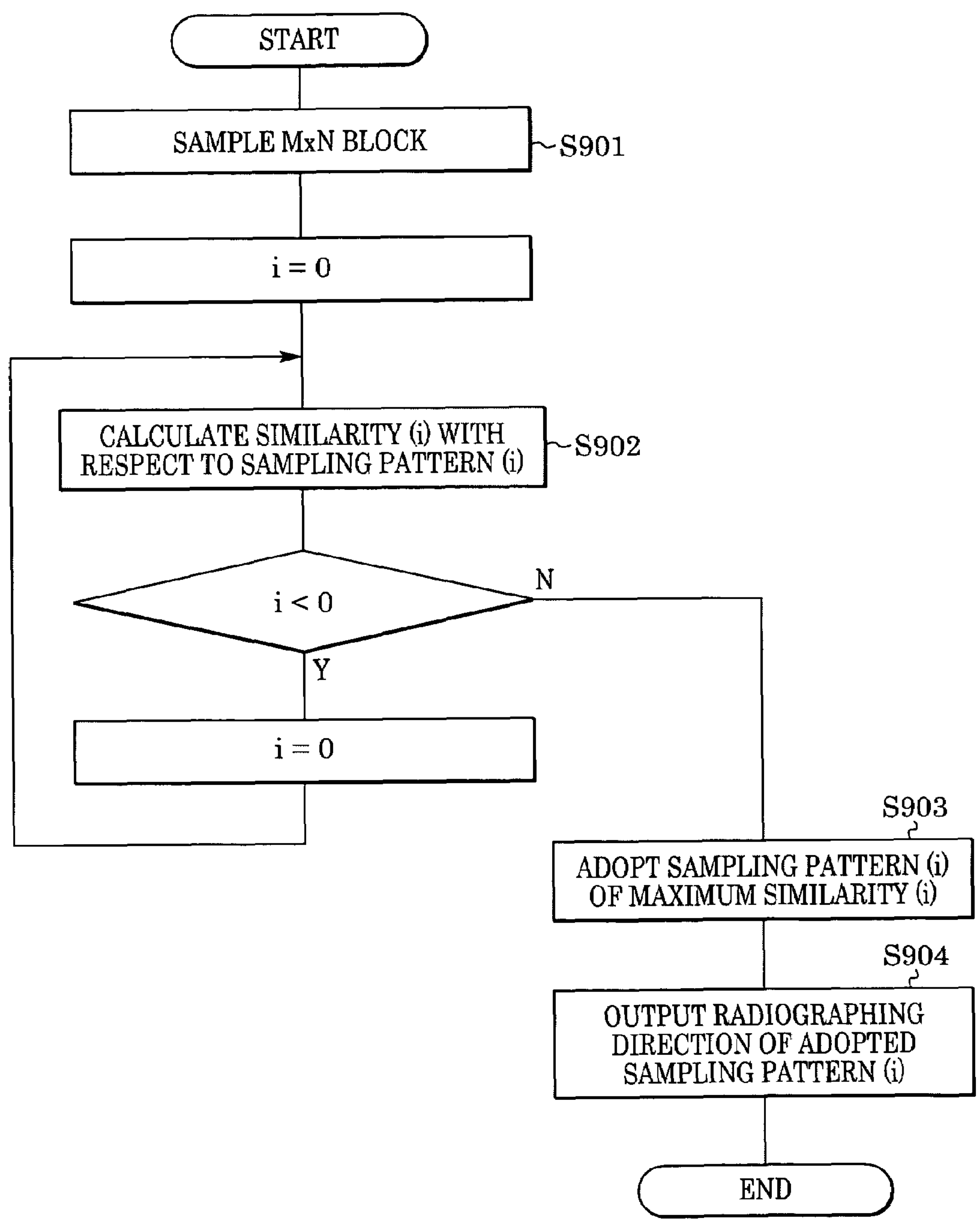
FIG. 9 is a flowchart showing a process performed by a radiographing direction acquisition circuit.
Figure 10:
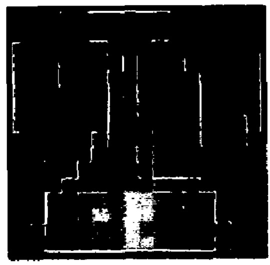
FIG. 10 shows a sampling pattern table used when the radiographing direction acquisition circuit performs pattern matching.
Figure 10:
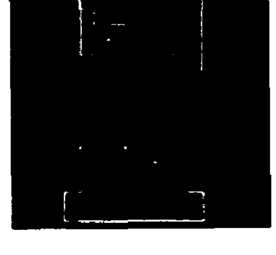

FIG. 8 is a flowchart showing a process performed in the second embodiment. FIG. 9 is a flowchart showing a process performed by the radiographing direction acquisition circuit 71. FIG. 10 shows a sampling pattern table used when the radiographing direction acquisition circuit 71 performs pattern matching.

After sequentially receiving the plurality of pieces of image data 401 to 40X processed by the preprocessing circuit 15 via the CPU bus 16 under the control of the CPU 17, the image processing circuit 20 acquires a radiographing direction of all or part of the received image data 401 to 40X by the radiographing direction acquisition circuit 71 (step S801). If part of the received image data 401 to 40X is used, image data is input to the radiographing direction acquisition circuit 71 every predetermined constant L to acquire each radiographing direction. Various methods for acquiring a radiographing direction are possible. In the second embodiment, a method for acquiring a radiographing direction using a pattern matching method, which is a basic image recognition method, as shown in FIGS. 9 and 10, is used.

Referring to the flowchart of FIG. 9, M×N blocks of the image data input to the radiographing direction acquisition circuit 71 are sampled (step S901). As a method of the sampling process, for example, the average in each block is used. As shown in FIG. 10, the image data is sequentially compared with sampling patterns prepared in advance each including an M×N block, and the similarity with each of the sampling patterns is calculated (step S902). For calculation of the similarity, for example, simple similarity S(x, i) corresponding to a concentration change of the whole image shown by the following equation is used:

$$S(x, i)=(x \cdot ci)/(\|x\| \cdot \|ci\|),$$

where x represents the sampled image data and ci represents the i-th sampling pattern. The simple similarity S(x, i) is between −1 and 1. The simple similarity S(x, i) becomes closer to 1 the closer the similarity achieved between x and i. Thus, the i-th sampling pattern having the maximum simple similarity S(x, i) is adopted (step S903). Consequently, a radiographing direction of the input image data can be acquired (step S904).

Also, the radiographing direction acquisition circuit 71 may be realized by an advanced method, such as a pattern matching method using the complex similarity by principal component analysis, a method using a neutral network having a learning function, or the like.

The representative image selection circuit 21 selects at least one representative image from among the plurality of pieces of image data (step S802). The representative image is selected in accordance with the radiographing direction of the image data acquired by the flowchart of FIG. 9. In the second embodiment, for example, representative images whose radiographing directions are 0 degree and 180 degrees are selected. In this case, the representative images 501 and 503 shown in FIG. 5 are selected.

For example, if six images close to 90 degrees or 270 degrees are selected as representative images, images including a large so-called through area in which an X-ray beam directly reaches the two-dimensional X-ray sensor 13 without penetrating the test object S can be obtained by radiography from substantially the side direction, which is close to 90 degrees or 270 degrees. Thus, accuracy in the irradiated area extraction circuit 22 provided downstream is achieved.

Processing performed by the irradiated area extraction circuit 22 (step S803), processing performed by the reconstruction area determination circuit 23 (step S804), and processing performed by the reconstruction circuit 24 (step S805) are similar to steps S202 to S204 shown in FIG. 2.

As described above, according to the second embodiment, a radiographing direction of image data can be acquired. Thus, accuracy in extraction of an X-ray irradiated area is improved and a stable CT reconstruction area is automatically determined.

Figure 11:
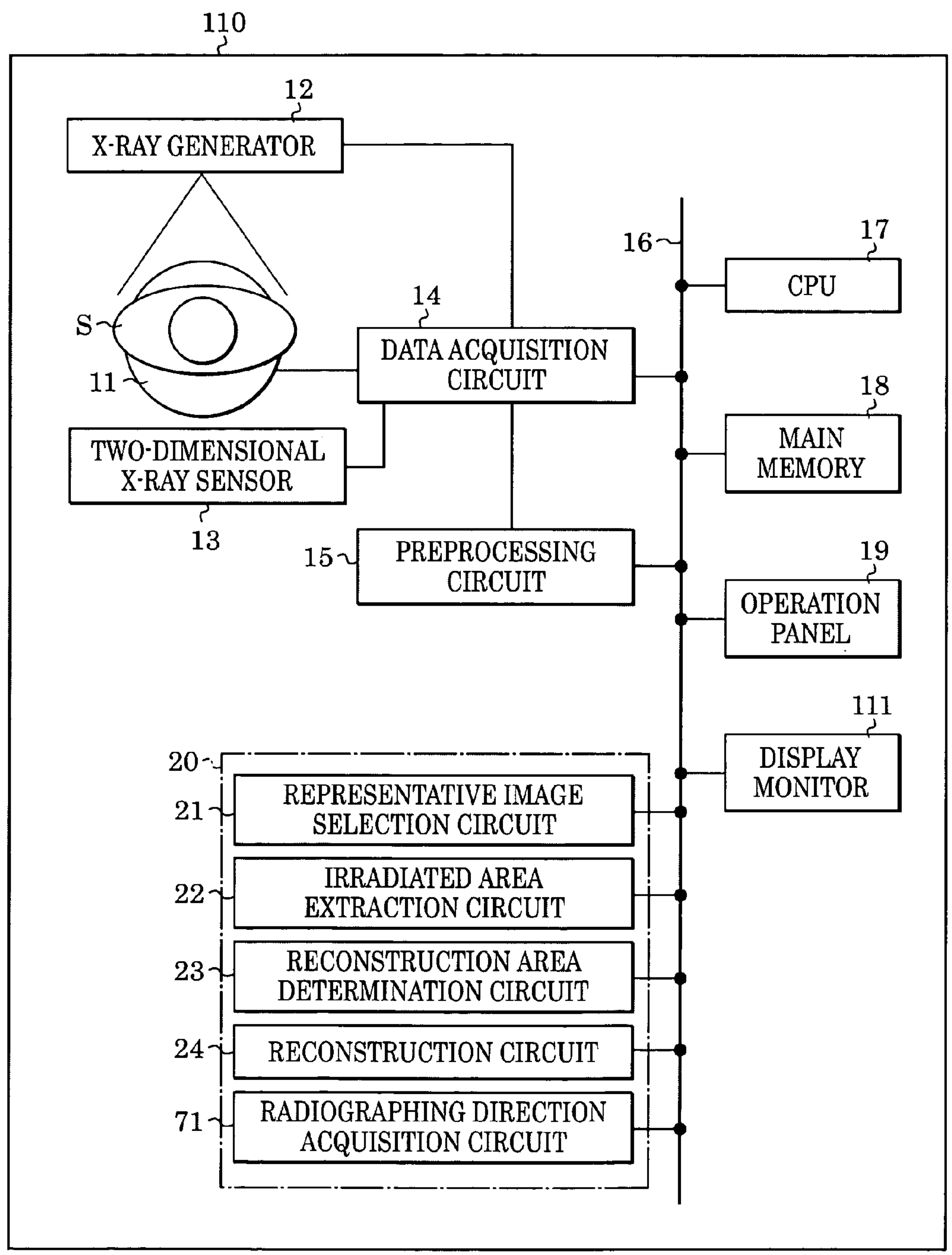
FIG. 11 shows the structure of a radiography apparatus according to a third embodiment of the present invention.

FIG. 11 shows the structure of a radiography apparatus 110 according to a third embodiment of the present invention. Compared with the radiography apparatus 70 according to the second embodiment, a display monitor 111 is added.

As in the second embodiment, the operations from radiation of an X-ray beam to transfer of image data are repeatedly performed while operating the rotating device 11, so that image data radiographed from different directions is sequentially transferred to the image processing circuit 20. In the third embodiment, the data acquisition circuit 14 acquires the current angle information from the rotating device 11, and transfers the information, together with corresponding image data, to the image processing circuit 20.

Figure 12:
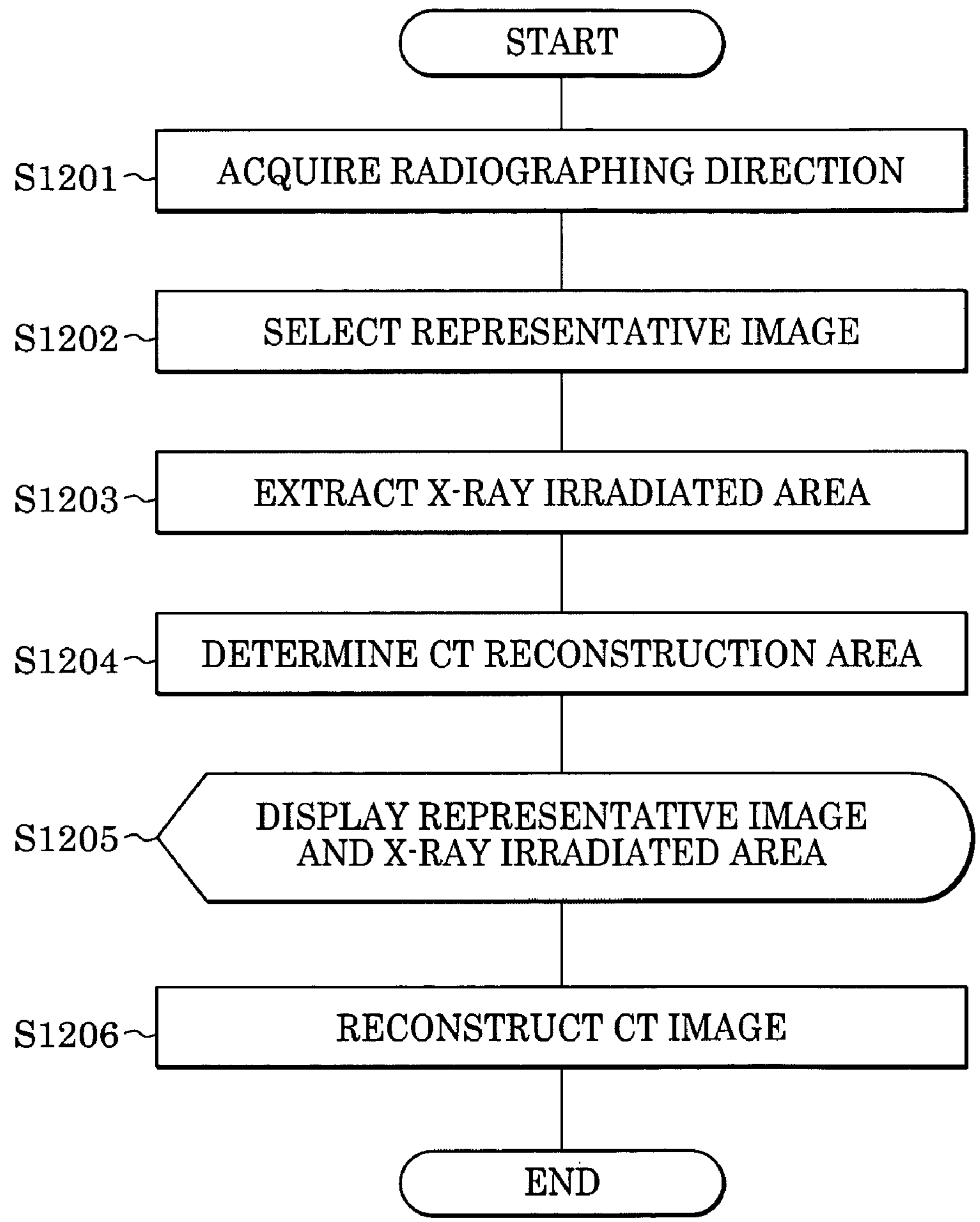
FIG. 12 is a flowchart showing a process performed in the third embodiment.
Figure 13:
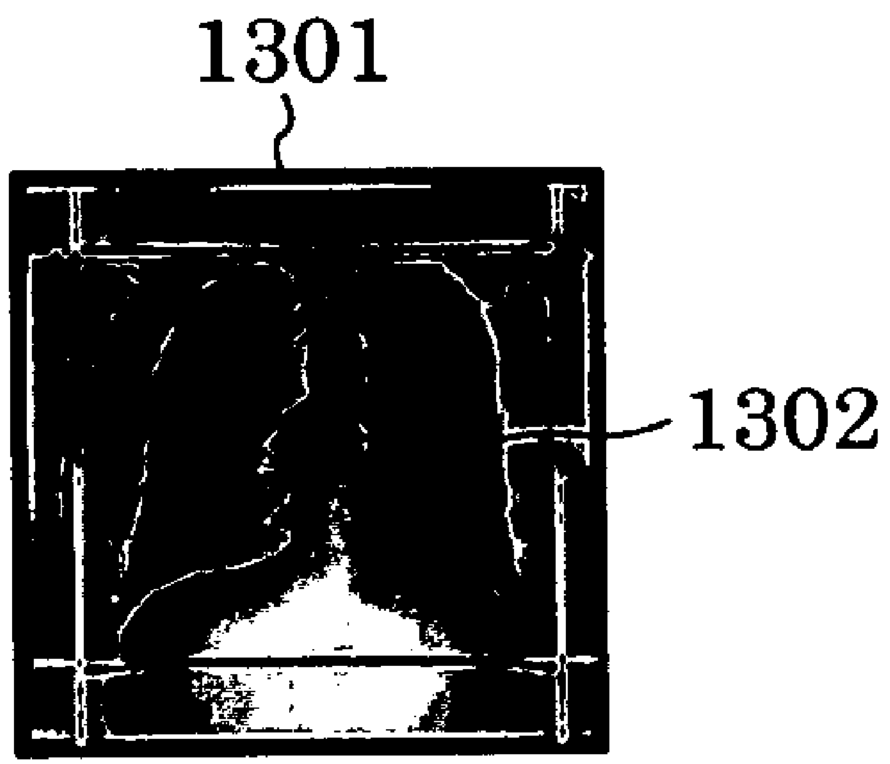
FIG. 13 shows an example of an image displayed on a display monitor.

FIG. 12 is a flowchart showing a process performed in the third embodiment. FIG. 13 shows an example of an image including a representative image 1301 and a CT reconstruction area 1302 displayed on the display monitor 111.

A process performed by the image processing circuit 20 will now be described with reference to the flowchart in FIG. 12. After sequentially receiving the plurality of pieces of image data 401 to 40X shown in FIG. 4 processed by the preprocessing circuit 15 and angle information acquired by the data acquisition circuit 14, the image processing circuit 20 acquires a radiographing direction of the received image data by the radiographing direction acquisition circuit 71 (step S1201). In the third embodiment, a radiographing direction at the start of radiography is determined in advance, so that a radiographing direction of image data is acquired from the received angle information.

For example, if the radiographing direction at the start of radiography is from the right of a test object to the left of the test object, a radiographing direction, such as diagonally from the right front to the left rear, can be acquired for angle information of 45 degrees, or a radiographing direction, such as from the rear to the front, can be acquired for angle information of 270 degrees. Although a radiographing direction is represented as described above for the sake of easy explanation, in practice, a radiographing direction is represented continuously using a numerical value or the like.

The representative image selection circuit 21 selects at least one representative image from among a plurality of pieces of image data (step S1202). The representative image is selected on the basis of the radiographing direction acquired by step S1201. In the third embodiment, for example, the representative image 1301 whose radiographing direction is from the rear to the front is selected.

Processing performed by the irradiated area extraction circuit 22 (step S1203) and processing performed by the reconstruction area determination circuit 23 (step S1204) are similar to steps S202 and S203 explained in the first embodiment. The image processing circuit 20 superimposes the CT reconstruction area 1302 determined by step S1204 on the representative image 1301 selected by step S1202, as shown in FIG. 13, to be displayed on the display monitor 111 (step S1205). Then, the reconstruction circuit 24 performs CT reconstruction processing (step S1206). This processing is similar to step S204 explained in the first embodiment.

As described above, according to the third embodiment, an automatically determined CT reconstruction area superimposed on general image data in the front direction as a scanogram is displayed on a monitor. Thus, a radiographer can immediately understand a CT reconstruction area. Also, since an X-ray irradiated area is extracted using only image data in a single direction, a stable CT reconstruction area can be automatically determined.

Figure 14:
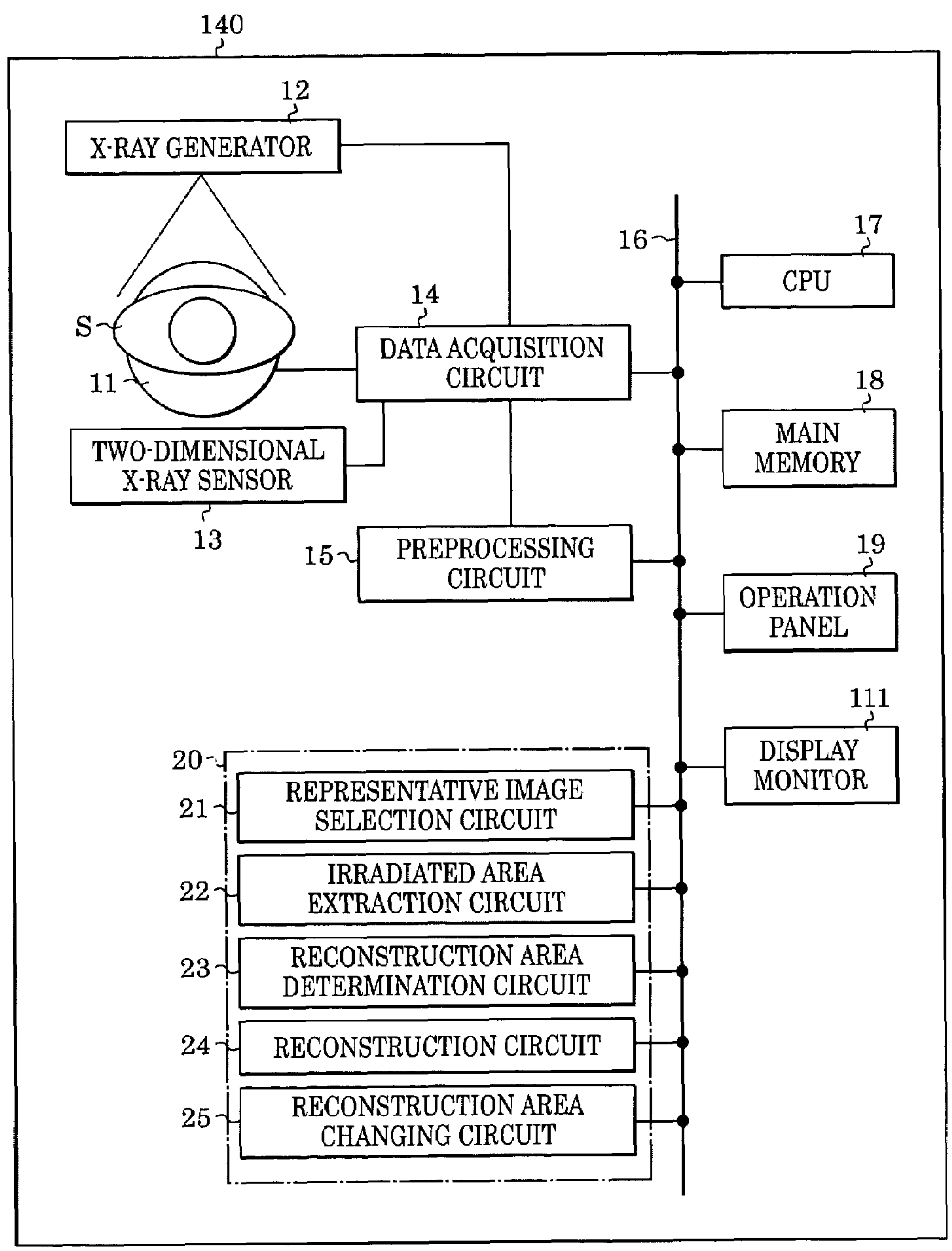
FIG. 14 shows the structure of a radiography apparatus according to a fourth embodiment of the present invention.

FIG. 14 shows the structure of a radiography apparatus 140 according to a fourth embodiment of the present invention. Compared with the radiography apparatus 110 according to the third embodiment, the radiographing direction acquisition circuit 71 is deleted and a reconstruction area changing circuit 141 is added.

As in the third embodiment, the operations from radiation of an X-ray beam to transfer of image data are repeatedly performed while operating the rotating device 11, so that image data radiographed from different directions is sequentially transferred to the image processing circuit 20. In the fourth embodiment, angle information is not acquired from the rotating device 11.

Figure 15:
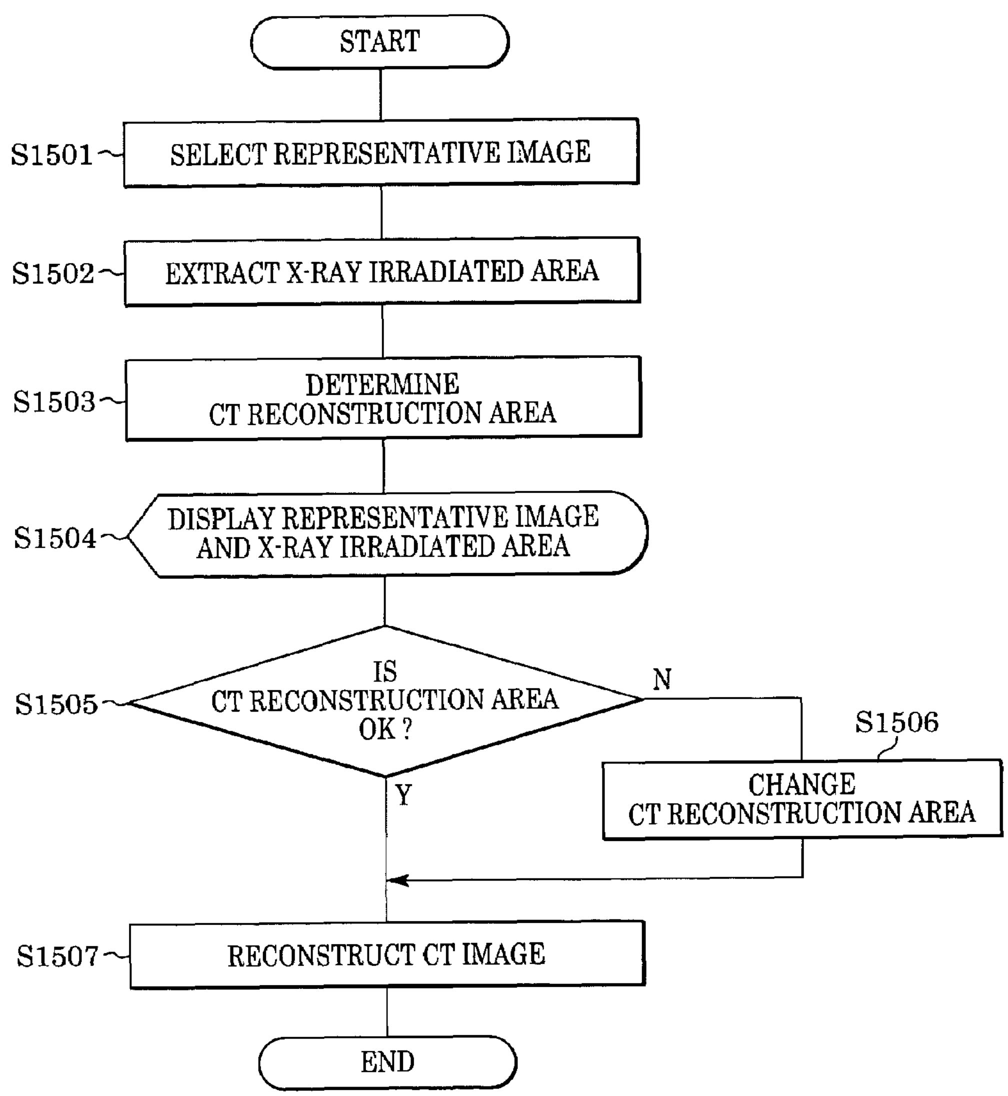
FIG. 15 is a flowchart showing a process performed in the fourth embodiment.
Figure 16:
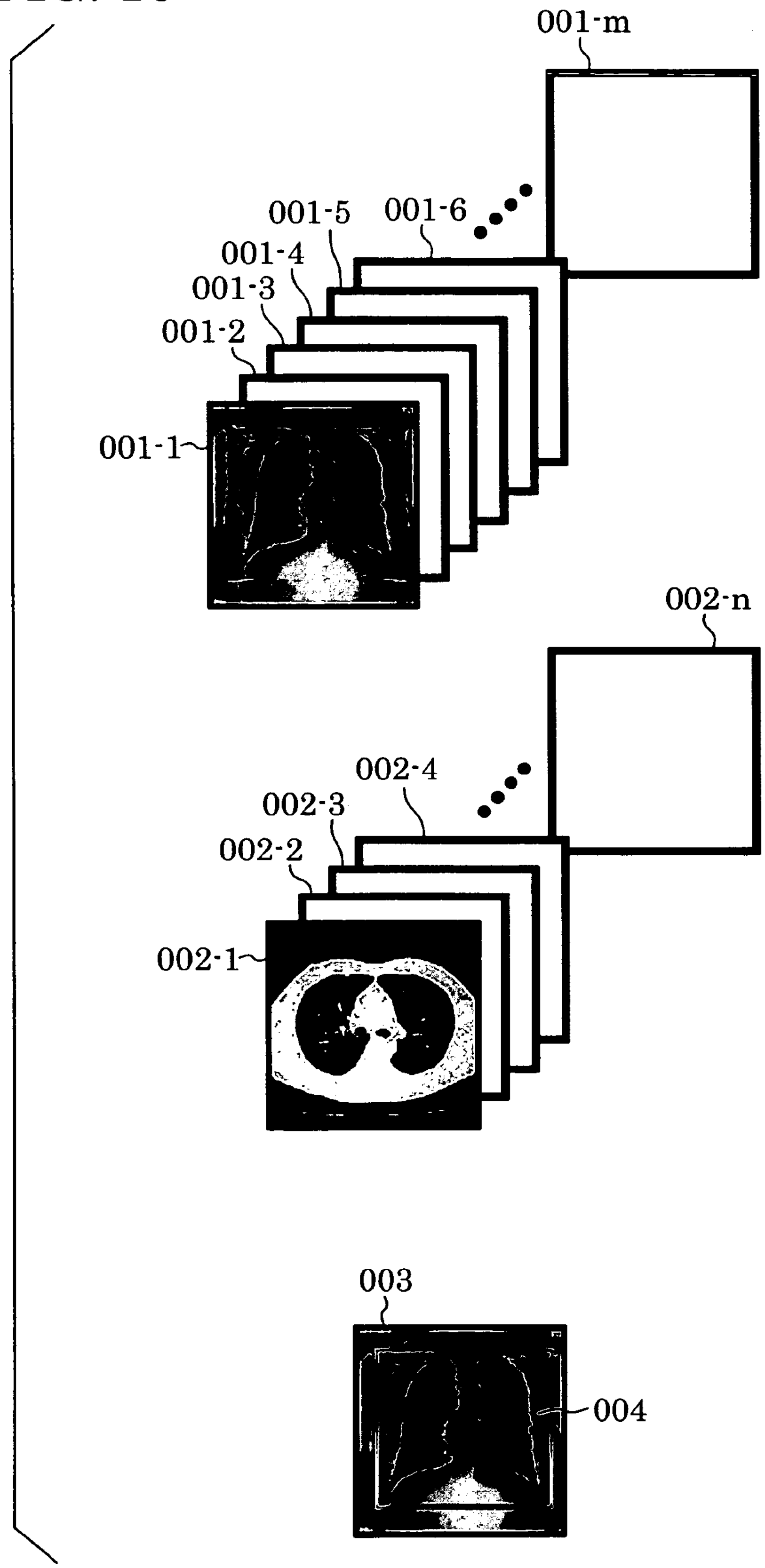
FIG. 16 schematically illustrates a known technology.

FIG. 15 is a flowchart showing a process performed in the fourth embodiment. After receiving the image data 401, which is a first frame, shown in FIG. 4 processed by the preprocessing circuit 15, the image processing circuit 20 unconditionally selects the image data 401 as a representative image by the representative image selection circuit 21 (step S1501).

Processing performed by the irradiated area extraction circuit 22 (step S1502), processing performed by the reconstruction area determination circuit 23 (step S1503), and processing for displaying the representative image and the X-ray irradiated area (step S1504) are similar to steps S202 and S203 shown in FIG. 2 and step S1205 shown in FIG. 12, respectively.

The image processing circuit 20 requires a radiographer to approve the CT reconstruction area 1302 displayed in step S1504 on the display monitor 111 shown in FIG. 13 (step S1505). If the automatically displayed CT reconstruction area 1302 is approved, the reconstruction circuit 24 performs CT reconstruction processing (step S1507) without changing the CT reconstruction area 1302. If the automatically displayed CT reconstruction area 1302 is not approved, the reconstruction area changing circuit 141 changes the CT reconstruction area 1302 (step S1506), and then, the CT reconstruction processing is performed (step S1507).

In step S1506 performed by the reconstruction area changing circuit 141, for example, a CT reconstruction area can be changed by manually resetting the CT reconstruction area using the operation panel 19 by a radiographer.

The reconstruction circuit 24 performs the CT reconstruction processing (step S1507). This processing is similar to the processing performed in step S204 shown in FIG. 2.

As described above, according to the fourth embodiment, an X-ray irradiated area is extracted using only image data in a single direction. Thus, a stable CT reconstruction area can be automatically set. Also, since a CT reconstruction area can be manually reset when a radiographer determines that an automatically set CT reconstruction area is improper, a reliable CT reconstruction area can be achieved. In this case, compared with a case where a CT reconstruction area is manually reset from the beginning, the number of operations performed by the radiographer is reduced. As a result of this, throughput of CT radiography is enhanced.

Furthermore, since a final determination of a reconstruction area is possible even before all the image is acquired, in other words, even before completion of radiography, as long as it is after acquisition of a first frame of image data, throughput of CT radiography is further enhanced.

As described above, a radiography apparatus that can perform CT reconstruction only on an area necessary for diagnosis in a short time without requiring a radiographer to perform a troublesome manual operation and that enhances throughput of CT radiography when CT images are acquired from a plurality of pieces of image data is provided.

MODIFICATIONS

Also, supplying program code 97 of software for realizing the functions (for example, functions realized by the flowcharts shown in FIGS. 2, 3, 8, 9, 12, and 15) of the foregoing embodiments to 98 a computer (central processing unit (CPU) or a micro-processing unit (MPU)) in an apparatus or a system connected to various devices for operating the various devices so as to realize the functions of the foregoing embodiments and operating the various devices in accordance with a program stored in the computer of the apparatus or the system is also included in the scope of the present invention.

In this case, the program code itself of the software realizes the functions of the foregoing embodiments. The program code itself and means for supplying the program code to the computer, for example, a storage medium 99 storing the program code, constitute the present invention.

The storage medium for storing the program code may be, for example, a floppy disk, a hard disk, an optical disk, a magnetic optical disk, a compact disk read-only memory (CD-ROM), a magnetic tape, a nonvolatile memory card, a ROM, and the like.

It is also obvious that the program code is included in the embodiments of the present invention not only when the functions of the foregoing embodiments are realized by executing the supplied program code by the computer but also when the functions of the foregoing embodiments are realized by the program code in cooperation with an operating system (OS) or other application software running on the computer.

Furthermore, after the supplied program code is stored in a function expansion board inserted into the computer or to a memory provided in a function expansion unit connected to the computer, a CPU or the like mounted on the function expansion board or function expansion unit performs all or a part of the actual processing in accordance with instructions of the program code so that the functions of the foregoing embodiments can be implemented by this processing.

As many apparently widely different embodiments of the present invention can be made without departing from the spirit and scope thereof, it is to be understood that the invention is not limited to the specific embodiments thereof except as defined in the appended claims.

What is claimed is:

1. A radiography apparatus comprising:

a radiation source for emitting radiation to a test object from different directions;

a two-dimensional X-ray sensor for sensing the radiation as a plurality of pieces of image data from the different directions;

a rotating unit configured to relatively rotate the test object and the radiation source;

an irradiated area extraction circuit configured to extract at least one irradiated area from the plurality of pieces of image data;

a determination circuit configured to determine a reconstruction area for computer tomography reconstruction based on at least the one irradiated area extracted by the irradiated area extraction circuit; and a reconstruction circuit configured to perform computer tomography reconstruction from the plurality of pieces of image data, except for image data which is not within the determined reconstruction area.

2. The radiography apparatus according to claim 1, further comprising:

an image selection circuit for selecting at least one piece of image data from the plurality of pieces of image data;

wherein the irradiated area extraction circuit extracts at least one irradiated area from at least one piece of selected image data.

3. The radiography apparatus according to claim 2, further comprising:

a radiographing direction acquisition circuit for acquiring information about a radiographing direction of the image data, wherein the image selection circuit selects the image data on the basis of the radiographing direction.

4. The radiography apparatus according to claim 2, wherein the image selection circuit selects image data that is first captured after start of radiography.

5. The radiography apparatus according to claim 3, wherein the image selection circuit selects image data whose radiographing direction is in a front direction or a side direction with respect to the test object.

6. The radiography apparatus according to claim 1, wherein the plurality of pieces of image data include the positions of the top, bottom, left, and right edges of X-ray irradiated areas, wherein the reconstruction area is based upon an average value of each position.

7. The radiography apparatus according to claim 1, wherein the plurality of pieces of image data includes a plurality of distances between the edges of an X-ray irradiated area and the X-ray irradiated area's center, wherein the reconstruction area is based upon the largest distance.

8. A radiation image processing method comprising:

an irradiated area extraction step of extracting at least one irradiated area from a plurality of pieces of image data by an irradiated area extraction circuit. obtained by radiographing a test object from different directions using a two-dimensional sensor;

a reconstruction area determination step of determining a reconstruction area for computer tomography reconstruction by a determination circuit, based on the at least one irradiated area extracted by the irradiated area extraction circuit; and a reconstruction step of performing, by a reconstruction circuit, the computer tomography reconstruction from the plurality of pieces of image data, except for image data which is not within the determined reconstruction area.

9. The radiation image processing method according to claim 8, wherein the plurality of pieces of image data include the positions of the top, bottom, left, and right edges of X-ray irradiated areas, wherein the reconstruction area is based upon an average value of each position.

10. The radiation image processing method according to claim 8, wherein the plurality of pieces of image data includes a plurality of distances between the edges of an X-ray irradiated area and the X-ray irradiated area's center, wherein the reconstruction area is based upon the largest distance.

11. A computer readable memory configured to store a program for Derforming a radiation image processing method, the method comprosing the steps of:

extracting an irradiated area from at least one piece of image data obtained by radiographing a test object from different directions using a two-dimensional sensor by using an extracting area computer code stored in a storage device;

extracting at least one irradiated area from the plurality of pieces of image data obtained by radiographing a test object from different directions using a two-dimensional sensor;

determining a reconstruction area for computer tomography reconstruction based on the at least one irradiated area extracted by using a determination computer code stored in the storage device; and determining the computer tomography reconstruction from the plurality of pieces of image data, except for image data which is not within the determined reconstruction area by using reconstruction computer code stored in the storage device.

12. A radiation image processing apparatus comprising:

an irradiated area extraction unit configured to extract at least one irradiated area from a plurality pieces of image data obtained by radiographing a test object from different directions using a two-dimensional sensor;

a reconstruction area determination unit configured to determine a reconstruction area for computer tomography reconstruction based on the at least one irradiated area extracted by the irradiated area extraction circuit; and a reconstruction unit configured to perform the computer tomography reconstruction from the plurality of pieces of image data, except for image data which is not within the determined reconstruction area.

13. The radiation image processing apparatus according to claim 12, wherein the plurality of pieces of image data include the positions of the top, bottom, left, and right edges of X-ray irradiated areas, wherein the reconstruction area is based upon an average value of each position.

14. The radiation image processing apparatus according to claim 12, wherein the plurality of pieces of image data includes a plurality of distances between the edges of an X-ray irradiated area and the X-ray irradiated area's center, wherein the reconstruction area is based upon the largest distance.

* * * * *